United States Patent [19]
Adams

[11] Patent Number: 5,311,449
[45] Date of Patent: May 10, 1994

[54] STERILIZABLE HAND-HELD PROGRAMMER/INTERROGATOR

[75] Inventor: Theodore P. Adams, Edina, Minn.

[73] Assignee: Angeion Corporation, Plymouth, Minn.

[21] Appl. No.: 674,132

[22] Filed: Mar. 25, 1991

[51] Int. Cl.⁵ .............................................. G06F 15/42
[52] U.S. Cl. ................... 364/514; 364/413.02; 364/708.1; 607/9
[58] Field of Search ............... 364/413.01, 413.02, 364/413.27, 514, 708; 128/419 PT, 419 PG

[56] References Cited

U.S. PATENT DOCUMENTS

| | | | |
|---|---|---|---|
| 4,291,375 | 9/1981 | Wolf | 364/483 |
| 4,295,468 | 10/1981 | Bartelt | 128/419 PT |
| 4,297,569 | 10/1981 | Flies | 70/283 |
| 4,561,443 | 12/1985 | Hogrefe et al. | 128/419 PT |
| 4,571,589 | 2/1986 | Slocum et al. | 128/419 PT |
| 4,681,111 | 7/1987 | Silvian | 128/419 PT |
| 4,712,179 | 12/1987 | Heimer | 364/413.01 |
| 4,768,229 | 8/1988 | Benjamin et al. | 380/20 |
| 4,809,697 | 3/1989 | Causey, III et al. | 128/419 PT |
| 5,123,419 | 6/1992 | Platt et al. | 128/419 PT |

Primary Examiner—Kevin J. Teska
Assistant Examiner—Jae H. Choi
Attorney, Agent, or Firm—Patterson & Keough

[57] ABSTRACT

Sterilizable hand-held programmer/interrogator for communication with an implanted defibrillator, including follow-up. An electromechanical key allows the programmer/interrogator to function fully as a data programmer and as a data interrogator. A removable electromechanical key controlled by a surgeon allows a limited number of programmable functions and only a certain amount of data to be revealed when the device is interrogated by the patient. Interrogated data from the programmer/interrogator can be linked directly to the surgeon via a modem.

18 Claims, 2 Drawing Sheets

STERILIZABLE HAND-HELD PROGRAMMER/INTERROGATOR

BACKGROUND OF THE INVENTION

1. Field of the Invention

The present invention pertains to an implantable medical device, and more particularly, pertains to a programmer/interrogator for use with an implanted defibrillator, and includes a removable key which allows either full or limited functions of the programmer/interrogator.

2. Description of the Prior Art

During a surgical procedure involving the implantation of a defibrillator, it is often necessary to program various parameters of the device while it is still in the sterile field of the operating room. The presently available programmers are fairly large instruments and are not sterilizable. Since the typical transmitting distance of the programmer is only a few inches, it is necessary to invade the sterile field in order to use it during the implant procedure. To accommodate this need for use in the operating room, a part of the programmer containing the transmitting/receiving antenna, called a wand, is connected to the programmer via a long umbilical cord. In some cases, the wand can be sterilized. In other cases, it is placed within a long sterile plastic bag to isolate the wand, and to allow the surgeon to handle it. In either case, the surgeon must rely on another person outside the sterile field to manipulate the controls at his direction. This situation invites error, as the surgeon is usually unfamiliar with the programmer and normally cannot see the controls or display. The umbilical cord is usually coiled and pulls on the wand in an unsuitable fashion towards the programmer.

Most programmers serve a dual purpose, to transmit program data to the implanted device, and to receive data interrogated from the implanted device. In the program data transmission situation, the surgeon is setting up a mode of therapy while in the latter case, the surgeon is monitoring the settings or reviewing interrogated performance data from the implanted device and patient. The monitoring mode is used primarily as a follow-up tool to evaluate the implanted device and patient during subsequent office visits. This mode is very important for patients who have an implanted defibrillator because there is no other means available for evaluating the condition or effectiveness of the device. Normally, patients would therefore have to schedule periodic and frequent visits to their surgeon to have the device checked and would have to visit the surgeon whenever they suspect any anomaly. There are home follow-up devices for defibrillator patients which rely on electrocardiographic (EKG) data, but such methods are not suitable for defibrillator patients. There are no existing home follow-up devices for defibrillator patients.

The present invention overcomes the deficiencies of the prior art by providing a sterilizable keyed programmer/interrogator for a defibrillator whose operating data can be interrogated and electronically relayed to a surgeon's office.

SUMMARY OF THE INVENTION

The general purpose of the present invention is to provide a single system which solves the two aforementioned problems previously discussed.

The general purpose of the present invention is a low cost, hand-held programmer/interrogator which can be supplied sterile with each implantable device, and therefore, can be used within the sterile field at the time of implant. Besides the necessary function control keys and display, the system contains an electromechanical "key" which, when in place, allows the device to function fully as a data programmer and data interrogator. As supplied, with the key in place, the device can program every parameter and is able to retrieve every available bit of data from the implanted device.

Retrieved data can be shown serially on the device display on two lines of sixteen characters each, or it can be transmitted through a serial port to a computer terminal or any other display terminal. The key is actually a jumper wire electromechanical tool which electromechanically fits into a serial port connector. When connected to another device, the programmer functions as a conventional wand for expanded capabilities.

When the key is removed, however, the device functions are changed such that either none or a very limited number of functions are programmable, and only certain data is revealed when the device is interrogated. This allows the device to be given to the patient to be taken home after the implant and used as a follow-up device and/or patient programmer.

In normal usage, the patient holds the device near the implanted defibrillator and simply presses the "interrogator" button. The device does not show data, but instead analyzes the data and displays a message to the effect that all is OK, or to call a surgeon and also includes a code number to help the surgeon identify the nature of the problem. The device holds in memory all of the interrogated data, including stored EKGs, so it can be retrieved later by the surgeon when the key is reinserted or when a display terminal is connected to the key-serial port.

In an optional configuration, the patient is also supplied with an auto-dialer/modem which has a well for holding the follow-up interrogator. After interrogating the implanted device and recording the data in its memory, the device or surgeon may instruct the patient to transmit the data to the surgeon. The patient simply places the programmer/interrogator in the holding well of the modem and presses a single button. The modem device then communicates with the programmer/interrogator via radio frequency (RF) telemetry and instructs it to dump its memory. The modem device would then call a preset phone number and format and transmit the data to the receiving modem in the surgeon's office.

According to one embodiment of the present invention, there is provided a sterilizable programmer/interrogator. A sealed enclosure includes an integral antenna, a receiver and a transmitter connected between the antenna and the microprocessor, a double row digital display panel, a plurality of control buttons or switches, a serial input-output port, and a key for engaging into the serial port.

One significant aspect and feature of the present invention is a self-contained programmer/interrogator.

Another significant aspect and feature of the present invention is an electromechanical key for the I/O port for differentiating of functions of the programmer/interrogator.

A further significant aspect and feature of the present invention is the combination use of a key and serial I/O port for the programmer/interrogator.

Still another significant aspect and feature of the present invention is a programmer/interrogator that can stand alone and connects to external devices.

An additional significant aspect and feature of the present invention is a programmer/interrogator that diagnosis problems and encode or decode messages for a surgeon.

Yet another significant aspect and feature of the present invention is a programmer/interrogator that can stand alone or can be used with a modem.

Having thus described the embodiments of the present invention, it is a principal object hereof to provide a sterilizable hand-held programmer/interrogator for use with a defibrillator.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
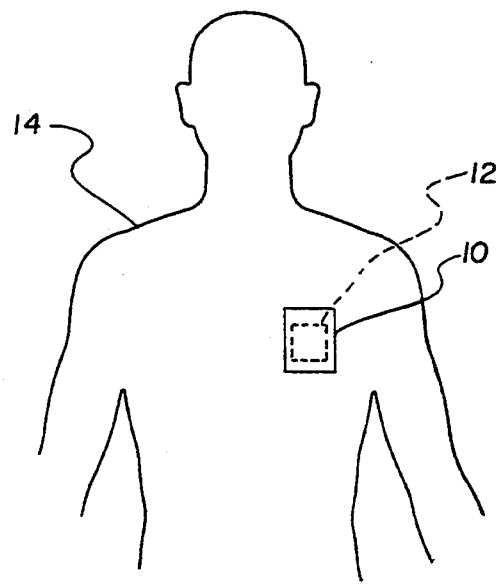
FIG. 1 a programmer/interrogator in use with a patient.

FIG. 1 illustrates a programmer/interrogator 10, the present invention, placed over a defibrillator 12 implanted in a patient 14. The defibrillator 12 includes internal transmitting and receiving circuits for communication through the patient's skin with the programmer/interrogator 10.

Figure 2:
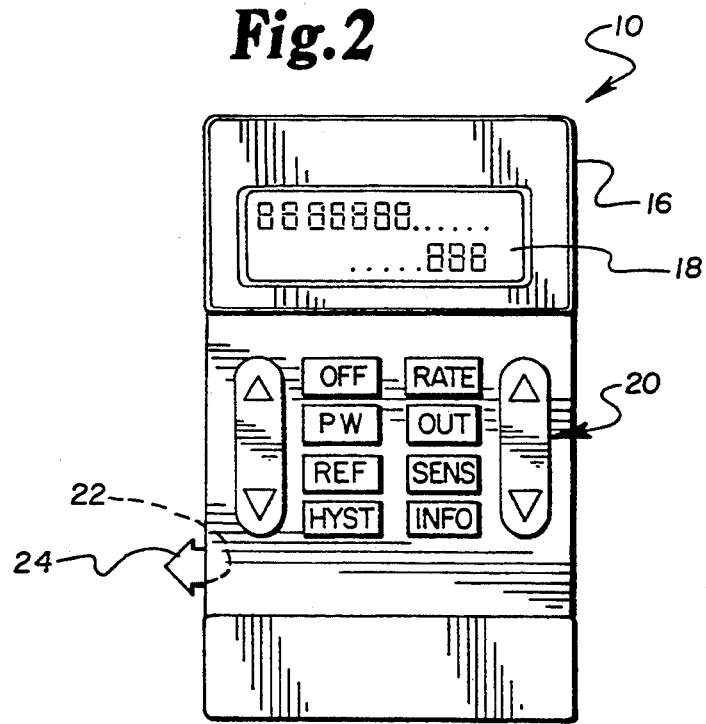
FIG. 2 illustrates a front view of the programmer/interrogator.

FIG. 2 illustrates a front view of a programmer/interrogator 10 including a sealed sterilizable enclosure 16, a 32 character digital display 18, a plurality of switch pads 20, a serial port 22, and a key 24 engaging the serial port 22. Programming algorithms are stored in memory connected to a microprocessor in the programmer/interrogator 10. The microprocessor is controlled by the key 24 and the switch pads 20.

The key 24 is controlled by the surgeon to allow programming of the implanted defibrillator 12 by the switch pads 20. Programming is accomplished by RF communication through the patient's skin by the RF circuits in the defibrillator 12 and in the programmer/interrogator 10. After programming, the key 24 is removed from the serial port 22, thereby decreasing the amount of programmability, namely the ability of the patient to program the device. The serial port can be located on either one of the sides or on the rear of the programmer/interrogator 10. A dummy key can then be inserted in place so as to protect the key slot. The patient, of course, can interrogate the programmer/interrogator 10 to receive a limited amount of user advisory information.

Figure 3:
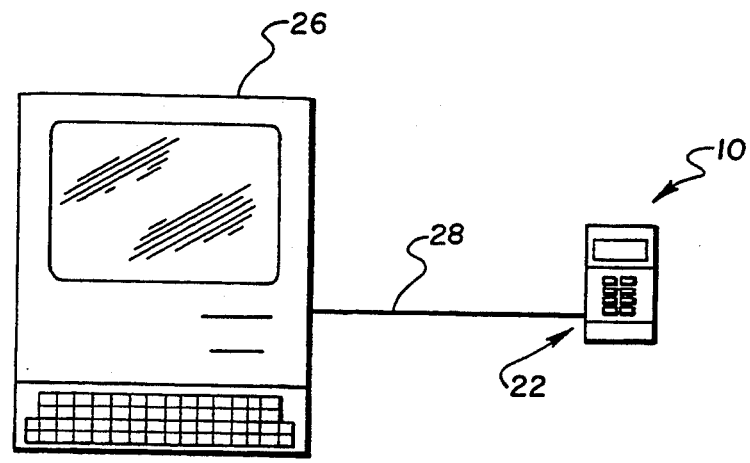
FIG. 3 illustrates the programmer/interrogator being used in conjunction with a computer; and, FIG. 4 illustrates the programmer/interrogator used with an auto-dialer/modem.

FIG. 3 illustrates the programmer/interrogator 10 being used in conjunction with a computer 26, such as a personal computer for expanded monitoring or programming capabilities. A cable 28 connects between the serial port 22 and the computer 26 to furnish data from the programmer/interrogator 10 which functions then as a conventional wand.

Figure 4:
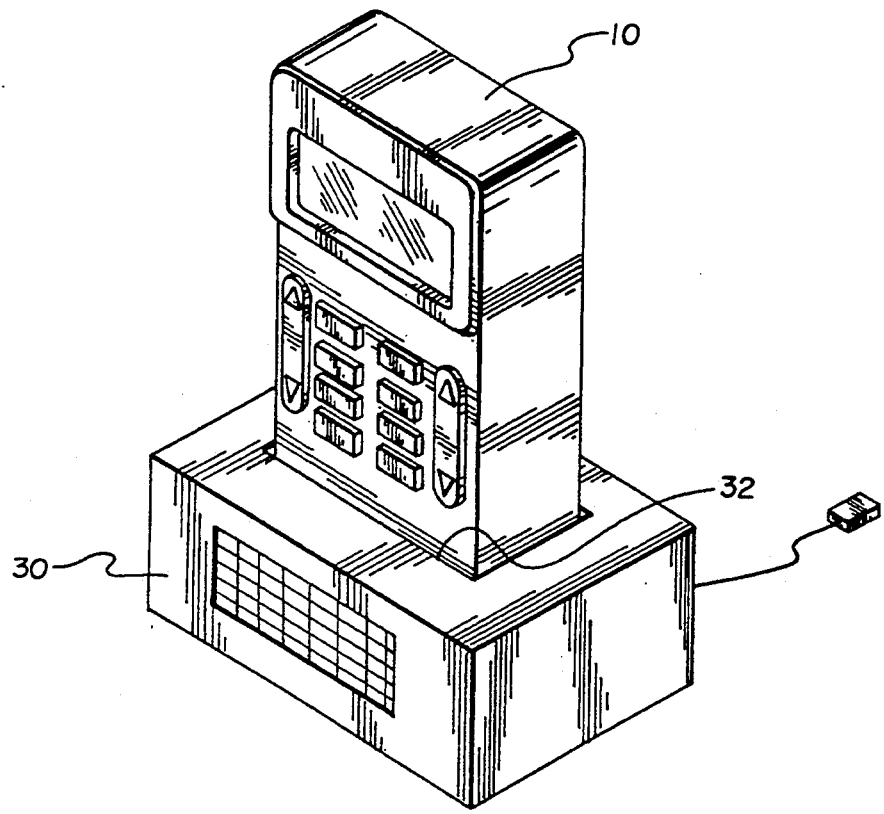

FIG. 4 illustrates the programmer/interrogator 10 in use with an auto-dialer/modem 30. The programmer/interrogator 10 is inserted into and is accommodated by a well 32 in the auto-dialer/modem 30. Interrogated data from the implanted device is transmitted from the memory to the surgeon upon command from the user patient. After communication of memory data, the data in the memory can be dumped and stored so that new and fresh monitoring can then be accomplished.

MODE OF OPERATION

The programmer/interrogator 10 can be used in a monitoring mode of FIG. 1, a programming mode of FIG. 2, a personal computer mode of FIG. 3, or a modem mode of FIG. 4.

Various modifications can be made to the present invention without departing from the apparent scope hereof. The teachings of the present invention for a defibrillator can also be extended to a pacemaker.

I claim:

1. A sterilizable hand-held programmer/interrogator for communicating with an implanted medical device in a sterile environment comprising:
    a sealed housing having dimensions such that the housing is small enough to be hand-held, the sealed housing including:
        processor means for controlling the operation of the programmer/interrogator;
        transceiver means connected to the processor means for transmitting and receiving data between the programmer/interrogator and the implanted medical device;
        memory means connected to the processor means for storing control algorithms for the processor means and data communicated with the implanted device;
        display means connected to the processor means for displaying operating information for the programmer/interrogator and data communicated with the implanted device; and
        switch pad means connected to the processor means for manually providing control and data information to the programmer/interrogator,
    such that the programmer/interrogator is sterilizable prior to use within the sterile environment to allow the programmer/interrogator to be used during the implantation of the implantable device in order to directly communicate with and program the implantable device without physically connecting the programmer/interrogator to another device.

2. The programmer/interrogator of claim 1 further comprising:
    port means connected to the processor means for providing communication with other processors via a cable connected to the port means either before or after the implantable device is implanted in the patient; and
    key means insertable into the port means while the programmer/interrogator is being used during the implantation of the implantable device for enabling a full operation mode of the programmer/interrogator, the key means also being sterilized prior to use within the sterile field.

3. The programmer/interrogator of claim 2 wherein removal of the key means from the port means disables the full operation mode of the programmer/interrogator and permits only a limited interrogation mode of operation of the programmer/interrogator.

4. The programmer/interrogator of claim 3 wherein the programming algorithms analyze the data communicated from the implanted device and provide a diagnostic code to be communicated to a physician when the programmer/interrogator is operating in the interrogation mode.

5. The programmer/interrogator of claim 1 further comprising:
   automatic modem means for providing telephonic communication between the programmer/interrogator and a remote processor, including:
   a body having a means for receiving the programmer/interrogator;
   means for connecting the automatic modem means to the port means of the programmer/interrogator;
   means for connecting the automatic modem means to a telephone line; and
   means for automatically controlling the transfer of data from the memory means of the programmer/interrogator to the remote processor.

6. A method for communicating with an implanted medical device in a sterile environment, the method comprising the steps of:
   (a) providing a programmer/interrogator in a sealed housing having dimensions such that the housing is small enough to be hand-held;
   (b) sterilizing the programmer/interrogator prior to use within in the sterile environment;
   (c) using the programmer/interrogator to directly communicate with and program the implantable device within the sterile environment during an implantation of the implanted device without physically connecting the programmer/interrogator to another device.

7. The method of claim 6 wherein the programmer/interrogator includes within the sealed housing:
   a processor that controls the operation of the programmer/interrogator;
   a transceiver connected to the processor to transmit and receive data between the programmer/interrogator and the implanted medical device;
   a memory connected to the processor to store control algorithms for the processor and data communicated with the implanted device;
   a display connected to the processor for displaying operating information for the programmer/interrogator and data communicated with the implanted device;
   a communication port connected to the processor that provides for communication with other processors via a cable connected to the port; and
   a switch pad connected to the processor for manually providing control and data information to the programmer/interrogator.

8. The method of claim 7 wherein step (c) comprises the steps of:
   (c1) sterilizing a key that enables a full operation mode of the programmer/interrogator;
   (c2) inserting the key into the communication port prior to using the programmer/interrogator during the implantation of the implantable device; and
   (c3) using the programmer/interrogator in the full operation mode to directly communicate with and program the implantable device within the sterile environment during the implantation of the implanted device.

9. The method of claim 8 further comprising the steps of:
   (c4) removing the key from the programmer/interrogator after the implantation of the implanted device; and
   (c5) providing the programmer/interrogator to the patient such that the programmer/interrogator operates in only a limited interrogation mode operable by the patient.

10. The method of claim 9 wherein the limited interrogation mode of step (c5) comprises the steps of:
    (c51) communicating with the implanted device to receive data from the implanted device;
    (c52) analyzing the data from the implanted device; and
    (c53) providing diagnostic information to be communicated to a physician.

11. The method of claim 10 wherein step (c53) is accomplished by displaying a diagnostic code on the display.

12. The method of claim 9 further comprising the steps of:
    (c6) using the programmer/interrogator to communicate with the implanted device to receive data from the implanted device;
    (c7) storing the data in the memory of the programmer/interrogator;
    (c7) providing a modem separate from the programmer/interrogator for establishing telephonic communication between the programmer/interrogator and a remote processor; and
    (c8) automatically controlling the transfer of data from the memory of the programmer/interrogator to the remote processor.

13. A method for allowing two separate users to communicate with an implanted medical device, the method comprising the steps of:
    (a) providing a programmer/interrogator that directly communicate with and program the implantable device during an implantation of the implanted device without physically connecting the programmer/interrogator to another device;
    (b) inserting a key into the programmer/interrogator prior to using the programmer/interrogator during the implantation of the implantable device to enable a full operation mode;
    (c) having a physician use the programmer/interrogator in the full operation mode to directly communicate with and program the implantable device during the implantation of the implanted device;
    (d) removing the key from the programmer/interrogator after the implantation of the implanted device to allow only a limited interrogation mode; and
    (e) providing the programmer/interrogator to a patient such that the programmer/interrogator operates in only the limited interrogation mode operable by the patient,
    such that the same device may be used by the physician to program and interrogate the implantable device during implantation and by the patient to only interrogate the implantable device after implantation.

14. The method of claim 13 wherein the programmer/interrogator includes within the sealed housing:
    a processor that controls the operation of the programmer/interrogator;

a transceiver connected to the processor to transmit and receive data between the programmer/interrogator and the implanted medical device;

a memory connected to the processor to store control algorithms for the processor and data communicated with the implanted device;

a display connected to the processor for displaying operating information for the programmer/interrogator and data communicated with the implanted device;

a communication port connected to the processor that provides for communication with other processors via a cable connected to the port; and a switch pad connected to the processor for manually providing control and data information to the programmer/interrogator.

15. The method of claim 14 wherein the key is inserted in the communication port to enable the full operation mode of the programmer/interrogator.

16. The method of claim 13 wherein the limited interrogation mode of step (e) comprises the steps of:

(e1) communicating with the implanted device to receive data from the implanted device;

(e2) analyzing the data from the implanted device; and (e3) providing diagnostic information to be communicated to a physician.

17. The method of claim 16 wherein step (e3) is accomplished by displaying a diagnostic code on the display.

18. The method of claim 16 wherein step (e) comprises the steps of:

(e1) using the programmer/interrogator to communicate with the implanted device to receive data from the implanted device;

(e2) storing the data in the memory of the programmer/interrogator;

(e3) providing a modem separate from the programmer/interrogator for establishing telephonic communication between the programmer/interrogator and a remote processor; and (e4) automatically controlling the transfer of data from the memory of the programmer/interrogator to the remote processor.

* * * * *